United States Patent [19]

Svendsen

[11] Patent Number: 5,472,325

[45] Date of Patent: Dec. 5, 1995

[54] SUCTION PUMP FOR DRAINING BODY FLUIDS FROM BODY CAVITIES

[75] Inventor: Gunnar N. Svendsen, Jyllinge, Denmark

[73] Assignee: UNO Plast A/S, Hundested, Denmark

[21] Appl. No.: 50,247

[22] PCT Filed: Jan. 17, 1992

[86] PCT No.: PCT/DK92/00013

§ 371 Date: Jul. 12, 1994

§ 102(e) Date: Jul. 12, 1994

[87] PCT Pub. No.: WO92/12740

PCT Pub. Date: Aug. 6, 1992

[30] Foreign Application Priority Data

Jan. 18, 1991 [DK] Denmark .................................. 0083/91

[51] Int. Cl.$^6$ .................................................. F04B 43/02
[52] U.S. Cl. .................................................. 417/437; 604/9
[58] Field of Search .................................. 417/478, 479, 417/437; 92/89, 90, 91; 604/9, 10, 11, 153

[56] References Cited

U.S. PATENT DOCUMENTS

| 3,111,125 | 11/1963 | Schulte | 604/9 |
| 3,127,846 | 4/1964 | Kerns | 604/153 |
| 3,496,872 | 2/1970 | Riester | 417/413 R |
| 3,588,293 | 6/1971 | Morales | 417/479 |
| 3,947,156 | 3/1976 | Becker | 417/437 |
| 4,290,346 | 9/1981 | Bujaw | 417/478 |
| 4,479,761 | 10/1984 | Bilstad et al. | 417/479 |
| 4,634,430 | 1/1987 | Polaschegg | 604/153 |
| 4,657,490 | 7/1987 | Abbott | 604/153 |
| 4,850,955 | 7/1989 | Newkirk | 604/9 |
| 5,002,471 | 3/1991 | Perlov | 417/413 |
| 5,152,753 | 10/1992 | Laguette | 604/153 |

FOREIGN PATENT DOCUMENTS

| 0270205 | 6/1988 | European Pat. Off. . |
| 1206966 | 5/1958 | France .................. 417/479 |
| 1812711 | 8/1969 | Germany . |
| 1146413 | 3/1969 | United Kingdom . |
| 1173071 | 12/1969 | United Kingdom . |

Primary Examiner—Richard A. Bertsch
Assistant Examiner—Peter G. Korytnyk
Attorney, Agent, or Firm—Watson, Cole, Grindle & Watson

[57] ABSTRACT

A suction pump is used for draining body fluids from body cavities and has a bottom portion (1) and a resilient pump body (2) with a domed shape. The pump also has an inlet valve (27) and an outlet valve (17). The pump stroke is provided by the elastic deformation of the pump body (2) towards the bottom (1) and the suction stroke is provided due to the elasticity of the pump body (2). In order to achieve only a small pump clearance volume the pump body (2) has a smooth inner surface and the bottom has a concave inner side (8) corresponding to the inner configuration of the pump body (2) when it has been deformed for starting the suction stroke of the pump.

8 Claims, 7 Drawing Sheets

SUCTION PUMP FOR DRAINING BODY FLUIDS FROM BODY CAVITIES

BACKGROUND OF THE INVENTION

The present invention relates to a suction pump for draining body fluids from body cavities, the suction pump comprising a bottom portion and a domed resilient pump body having a substantially smooth inner surface, the pump body being connected to the bottom portion along its rim and forming a pumping chamber between the bottom portion and pump body, which suction pump further comprises an inlet valve and an outlet valve, the resilient pump body being resiliently deformable by manual action from its domed configuration towards the bottom portion for the provision of the pressure stroke of the suction pump and due to its elasticity returning to its domed configuration when relieved for the provision of the suction stroke of the pump.

A pump of the type mentioned above is disclosed in EP patent application No. 87307362.1 (publication No. 0270205). The domed pump body of the noted pump has a flat top which may be supported along its inner surface by means of two sets of intersecting ridges and the bottom portion is flat and may be provided with a set of upwardly extending ridges. In its deformed state the bottom and the inner surface of the pump body are spaced, and hence the pump has a large pump clearance volume, which means that only a relatively small part of the pump chamber is used in the pumping operation. The prior art pump is implantable and serves to transport body fluid from one cavity of the body into another when activated. Furthermore, the ridges of the pump body, if provided, serve to quickly return the pump body to its starting position. Similar pumps having an internally smooth domed pump body and a flat bottom portion are disclosed in GB 1,146,413 and GB 1,173,071.

SUMMARY OF THE INVENTION

It is the object of the present invention to provide a pump of the above-mentioned type in which the pump chamber is utilized so efficiently that the pump obtains a large capacity in relation to its size and which allows the suction pressure produced by the pump to be maintained for relatively long periods between consecutive pressure strokes, the object being obtained according to the invention by the bottom portion having a concave portion which substantially corresponds to the inner configuration of the pump body in the deformed state thereof. As a result, it is possible to manually place at least the major part of the inner surface of the pump body in the deformed position thereof close to or in contact with the concave part of the bottom portion, thereby forming a very small clearance volume in the pump, and consequently it is possible to use approximately the entire volume of the pump chamber for the pumping function, thereby allowing the suction pressure to be maintained for relatively long periods.

In tests forming the basis of the present invention it was found that if the inner surface of the pump body according to a preferred embodiment of the invention in the domed state of the pump body substantially has the form of a spherical segment, the suction pressure produced by the pump will only vary relatively little during the suction stroke, i.e., in the period during which the pump body returns from its deformed state to its domed configuration.

In a preferred embodiment of the pump according to the invention the spherical segment has an arc measure ranging between about 100° and 140°, expediently between 110° and 130°, and preferably being about 120°.

A further embodiment of the pump according to the invention is characterized in that at its top the spherical segment has a slightly smaller radius of curvature than at its sides. This embodiment has been found to provide a satisfactory equalization of the variations in pressure which may occur during the suction stroke.

According to a still further embodiment of the pump of the invention the inlet valve and the outlet valve are offset in relation to the rim of the pump body and connected to the pump chamber through channels in the concave portion of the bottom portion. This results in that the valves and the inlets of the valves are prevented from hindering the aimed deformation of the pump body.

The invention will now be explained in further detail with reference to the drawings.

DETAILED DESCRIPTION OF THE PREFERRED EMBODIMENT

Figure 6:
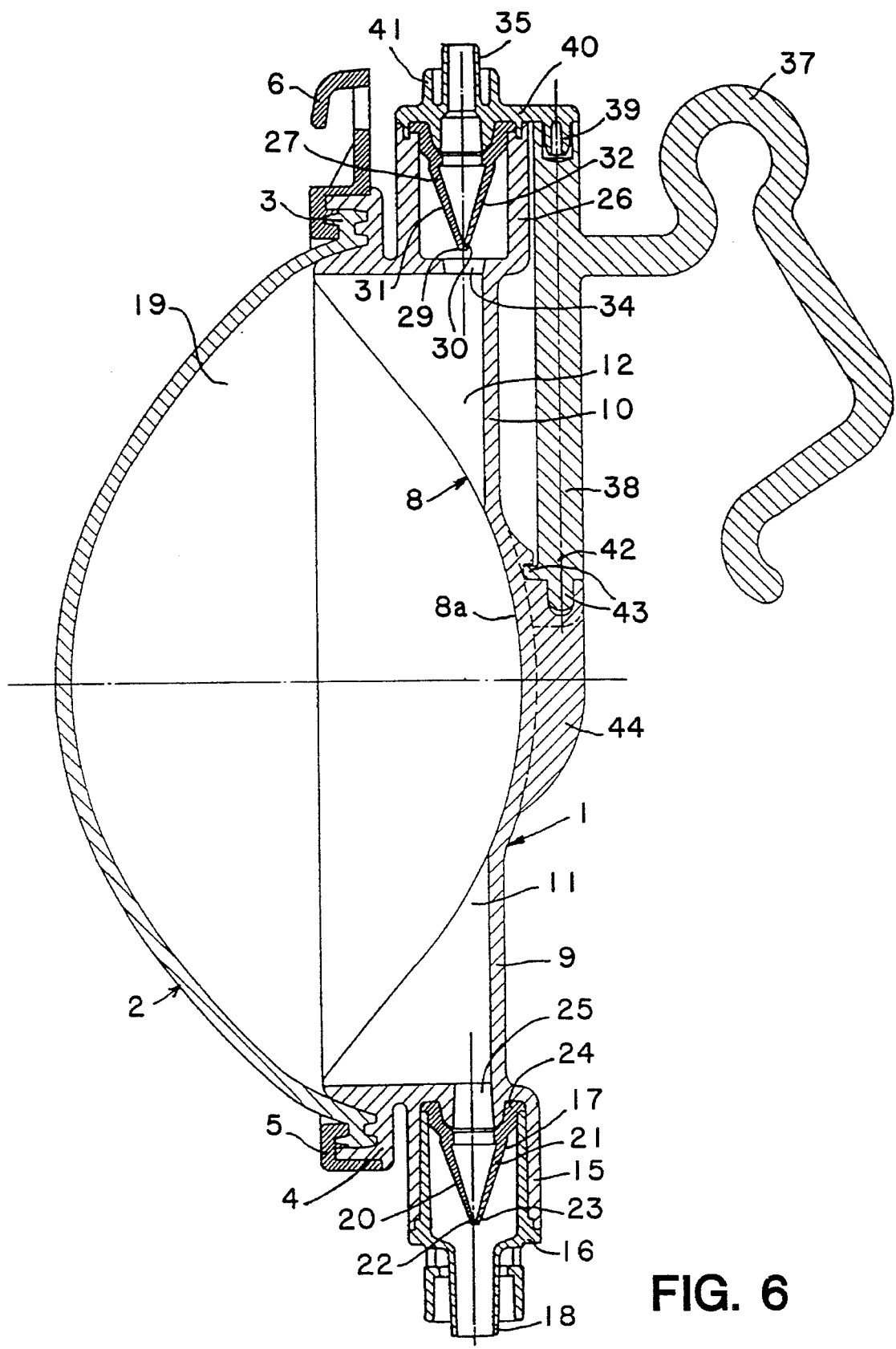
FIG. 6 shows a vertical sectional view of the pump shown on an enlarged scale.

In the drawings 1 designates a bottom portion of the pump shown and 2 a pump body. The pump body has a domed configuration and substantially the form of a spherical segment. The inner surface of the pump body is substantially smooth as will appear from FIG. 6, and along the circumference of the pump body a bead construction 3 is provided which is embedded in a rim portion 4 of the bottom portion, as will also appear from FIG. 6, the rim portion being profiled so as to correspond to the bead construction 3. The latter is kept in position in relation to the rim portion 4 by means of a holding ring 5 running along the entire circumference of the pump body 2 and being provided at its top with a suspension hook 6. Additional hooks 6a and 6b are provided at either side of the hook 6.

The bottom portion 1 has substantially the form of a cup 7, the inner surface of the cup having a concave configuration along the portion 8 of the bottom portion located within the rim portion 4.

Figure 1:
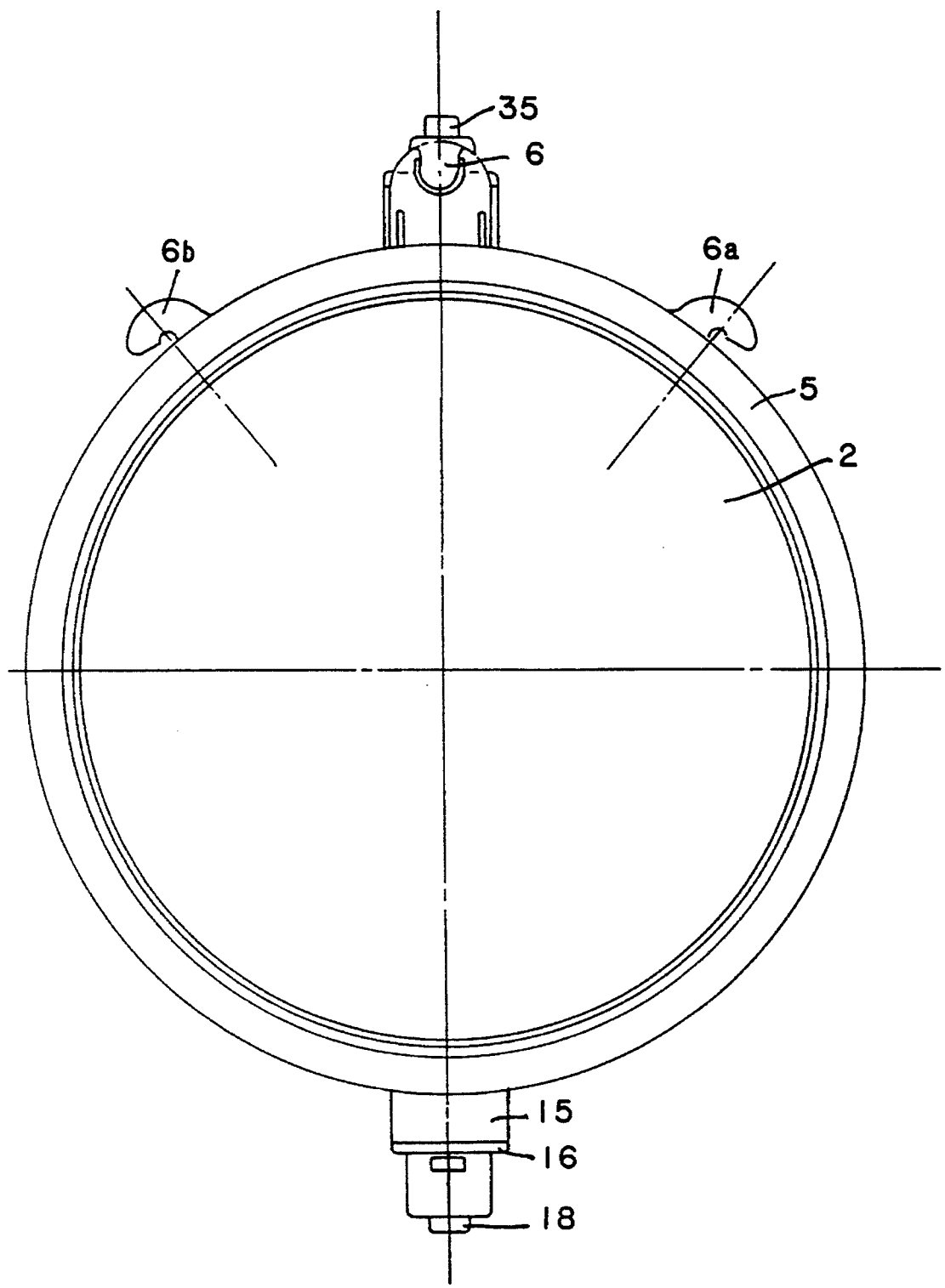
FIG. 1 shows a front view of an embodiment of the pump according to the invention.
Figure 2:
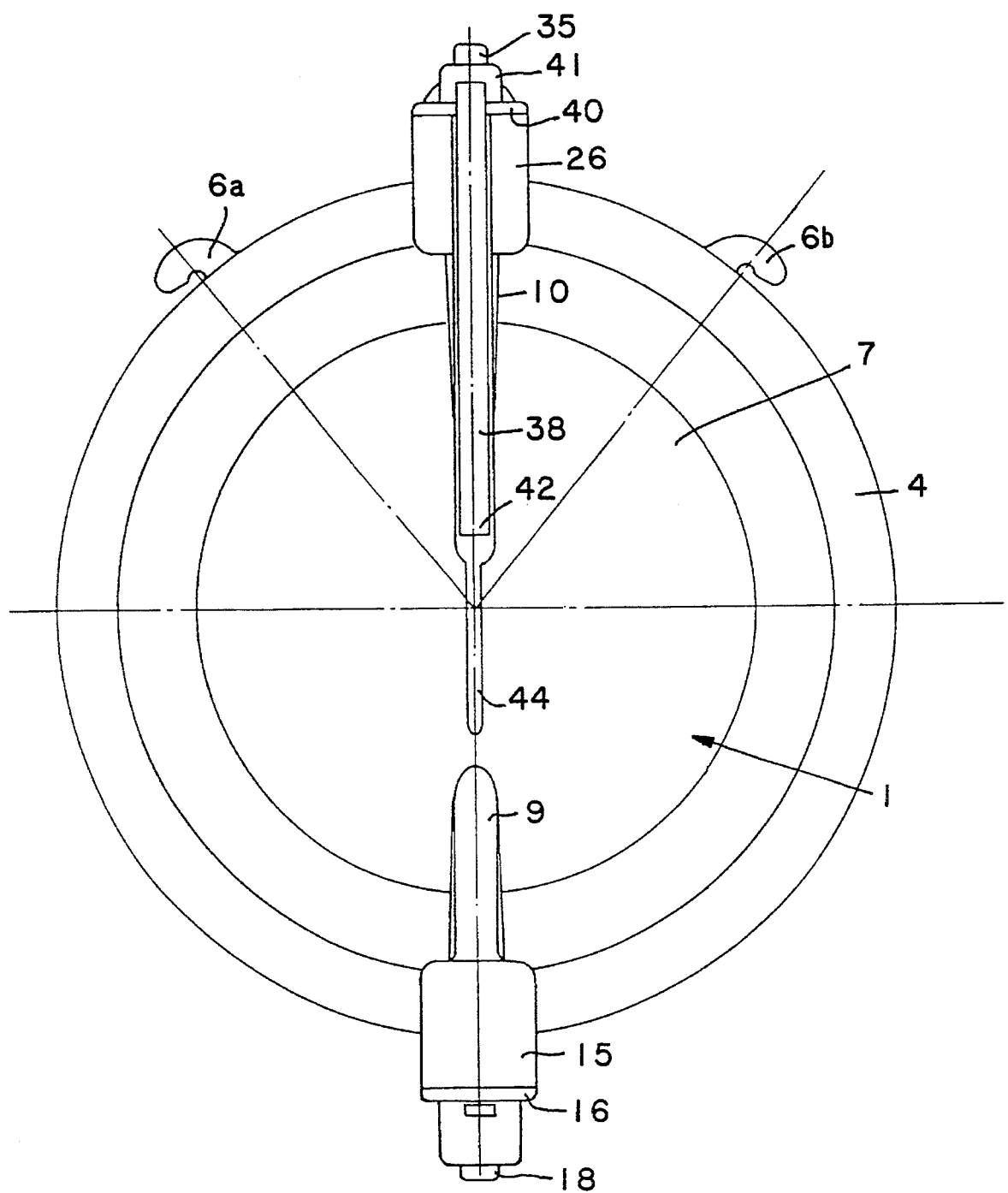
FIG. 2 shows a rear view of the pump of FIG. 1.
Figure 3:
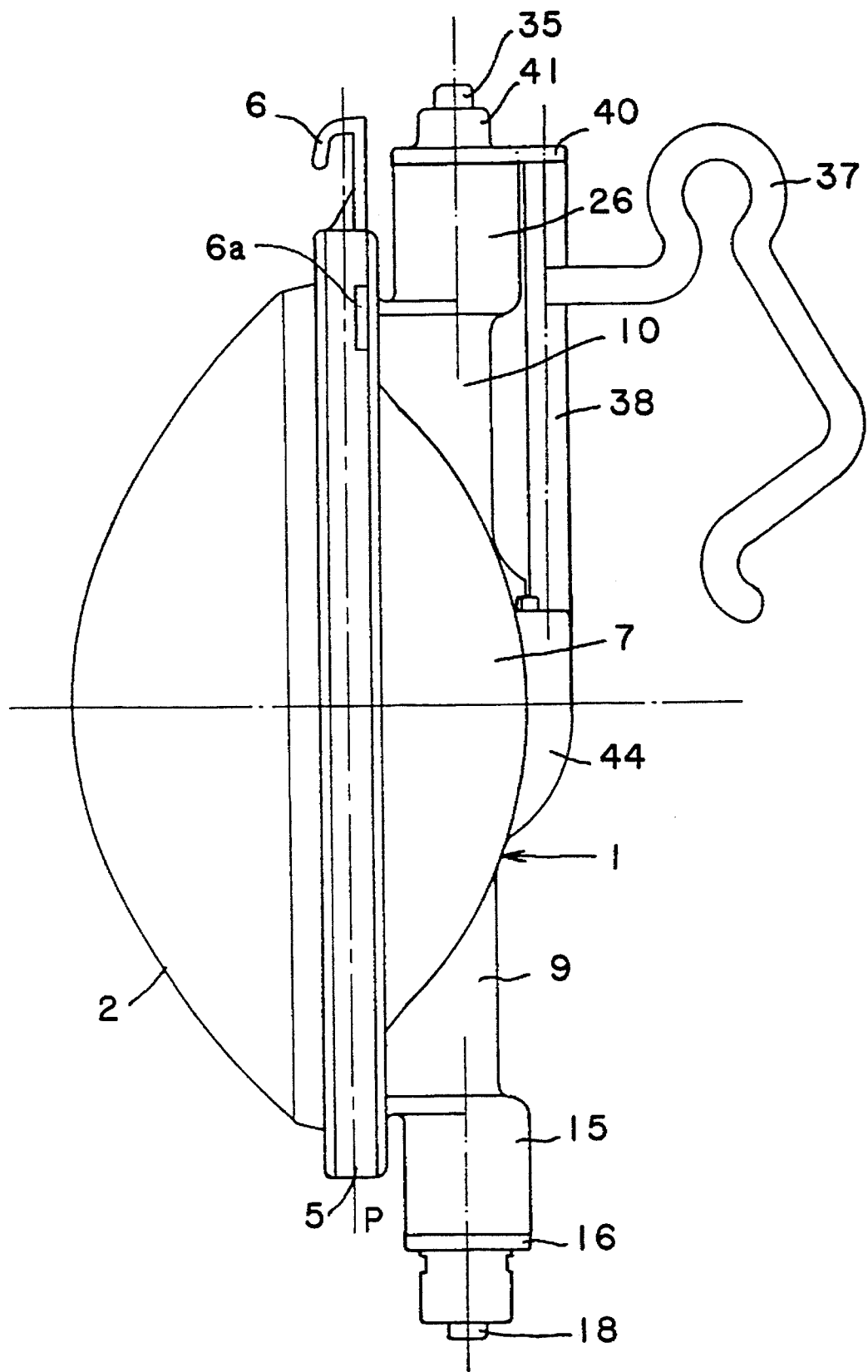
FIG. 3 shows a side view of the pump of FIG. 1.
Figure 4:
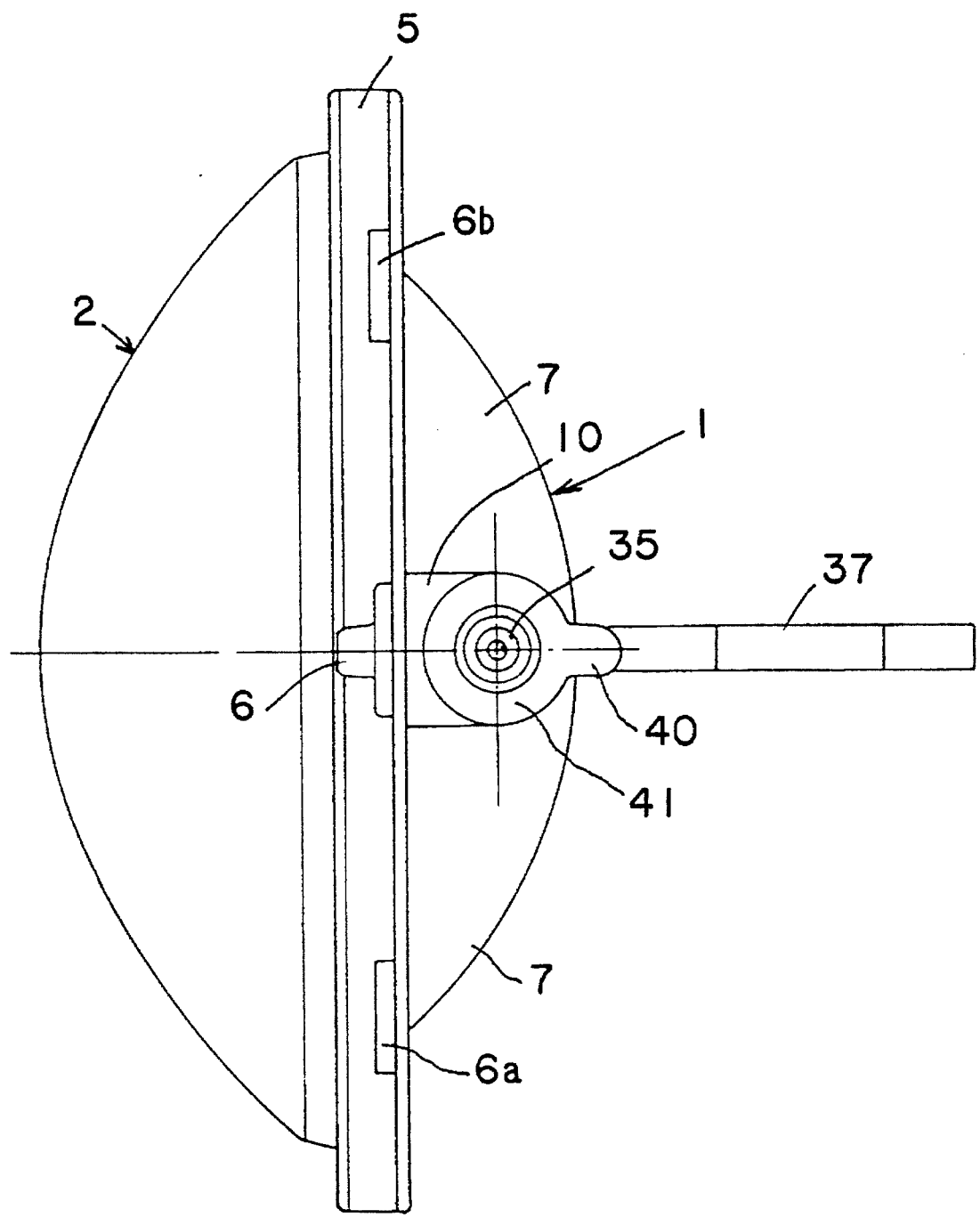
FIG. 4 shows a top view of the pump of FIG. 1.
Figure 5:
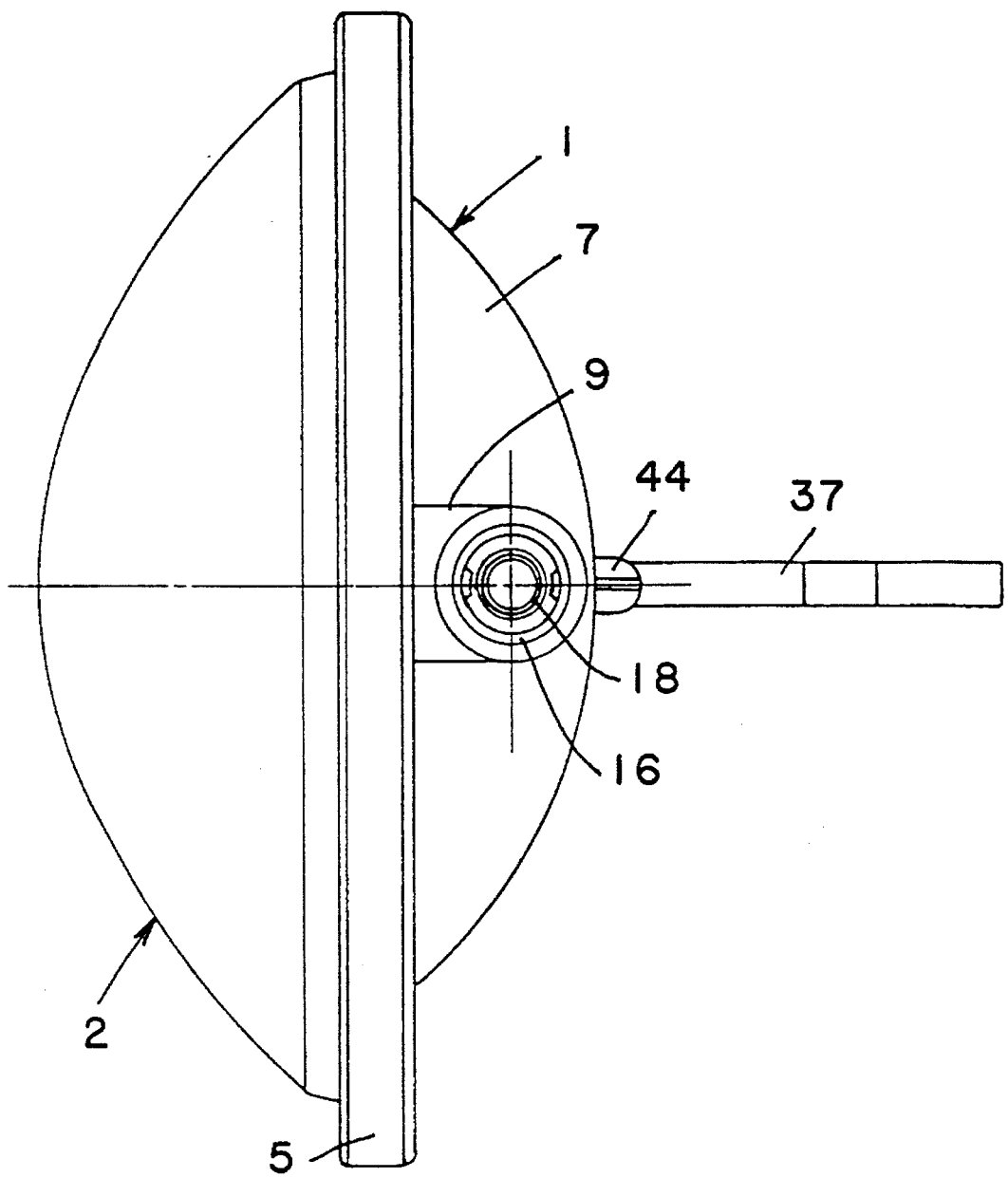
FIG. 5 shows a bottom view of the pump of FIG. 1.

The back of the cup 7 has two bulges 9 and 10, respectively, cf. FIG. 3, which extend flush with each other along a diameter of the cup. These bulges substantially have a U-shape and thus form internal channels 11 and 12, respectively, FIG. 6, which debouch along the concave inner surface of the portion 8. At the bottom the bulge 9 is provided with a collar 15 which is offset on one side of a center plane P defined by the rim of the pump body and comprises therein a valve holder 16 for an outlet valve 17. The holder 16 is provided with a nozzle 18 which is intended for mounting of a hose which is connected to a collection reservoir. The valve 17 only allows flow from the pump chamber 19 formed between the bottom portion 1 and the pump body 2. The valve is made of an elastic plastics material and has a tubular form at the top which downwardly passes into converging sides 20, 21 having adjoining downward facing edges 22, 23, which in case of overpressure in the pump chamber 19 are moved away from each other to allow discharge of fluid from the pump chamber. In case of underpressure in the pump chamber the edges 22, 23 are pressed together.

At its interior end the valve 17 has a circumferential flange 24 which is maintained by the corresponding upward facing edge of the holder 16. The valve 17 communicates with the channel 11 through an aperture 25 and the width of the channel 11 (as seen perpendicularly to the plane of the drawing in FIG. 6) corresponds substantially to the diameter of the aperture 25, the channel 11 thus being very narrow.

At the top the bulge 10 is provided with an inlet valve corresponding substantially to the outlet valve described above and consisting of a collar 26 in which a valve 27 having the same construction as the valve 17 is mounted, but which serves as an inlet valve, the edges 29,30 at the ends of the side walls 31, 32 of the valve turning inwards towards the pump chamber 19. The inlet valve is offset backwards in relation to the rim of the pump body and communicates with the channel 12 through an aperture 34, and the width of the channel 12 (seen perpendicularly to the plane of the drawing in FIG. 6) corresponds substantially to the diameter of the aperture.

The inlet valve is also provided with a nozzle 35 which is intended for securing one end of a connecting hose, the other end of which is coupled to a drainage tube in which a underpressure is generated after it has been positioned in the body cavity to drain the body cavity of body fluids. It will immediately be understood that the suction pressure in the pump chamber causes the inlet valve to be opened and the overpressure in the pump chamber causes the valve to be closed.

The pump shown is provided with a suspension arrangement 37 in the form of a hook, which, e.g., can be suspended from a hospital bed or equipment provided therefor. The hook is provided with a shank 38 having its upper end provided with a hole in which a spigot 39 engages on a protrusion 40 on the valve holder 41, whereas the lower end 42 of the shank is supported by means of a cam arrangement 43 engaging with recesses in a projection 44 on the outside of the bottom of the cup approximately at the centre of the latter. The cam arrangement is arranged in a manner which allows the hook 37 to be swung to one side or the other towards the pump so as to take up only little space. At the position shown in the drawing the hook is maintained by the elastically releasable engagement of one of the cams in the cam arrangement with a corresponding recess in the projection 44.

Between the bulges 9, 10 the interior of the bottom portion has substantially a spherical segment-shaped surface 8a.

As mentioned above, the inner surface of the pump body 2 has approximately the configuration of a spherical segment. In the embodiment shown in the drawing the spherical segment has a central angle of about 120°, but it may vary between 100° and 140°, expediently between 110° and 130°.

In the embodiment shown in the drawing the pump body does not have the exact form of a spherical segment, the radius of curvature at the top of the pump body being slightly smaller than the radius of curvature along the sides of the pump body.

The concave inner surface of the portion 8 extends approximately along a central arc measure of about 115°. It is noted that this inner surface does not have the exact form of a spherical segment either, the inner side also having a slightly smaller radius of curvature along its centre area 8a than along its sides. The arc measure of the inner surface of the portion 8 may also vary, expediently between 95° and 135°, preferably between 105° and 115°.

Figure 7:
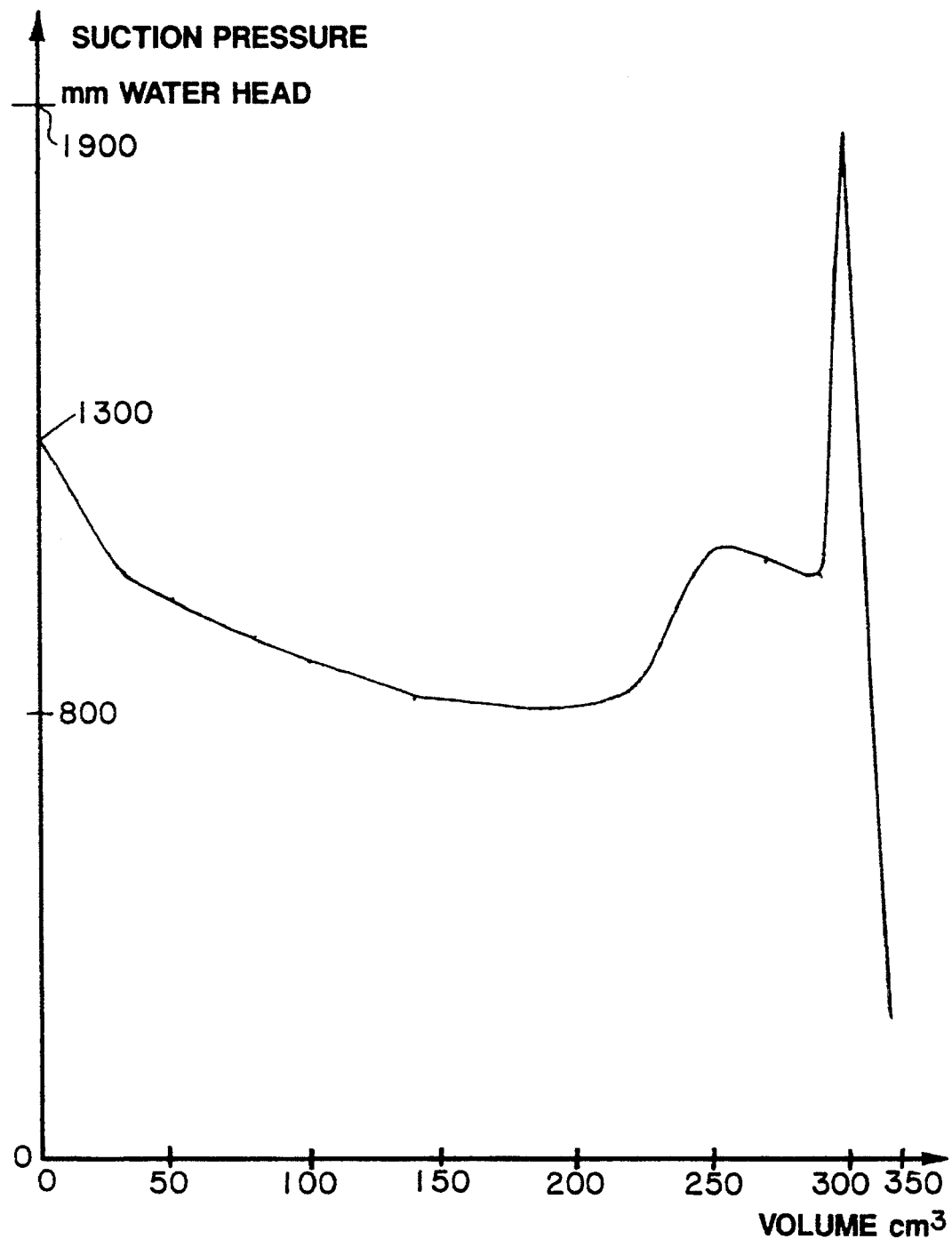
FIG. 7 shows a graph illustrating variations in the suction pressure as a function of the volume of the pump chamber during the suction stroke.

The pump shown operates in the following manner:

After the above-mentioned drainage tube has been installed and the pump has been connected to the collection reservoir as explained above, the pump body 2 is manually pressed inwards. The configuration of the inner surface of the pump body and the configuration of the inner surface of the portion 8 allow the pump body to be pressed into close engagement with the inner surface of the portion 8 so that a pump clearance volume is formed corresponding substantially to the volume of the channels 11,12, which are relatively narrow as explained above. When relieved the pump body 2 gradually returns to the shape shown in FIG. 6, during which it is removed from the inner surface of the portion 8 while producing a constant suction. FIG. 7 shows variations in the suction pressure as a function of the increase in the volume of the pump chamber during the suction stroke, and from the figure it appears that at the beginning of the suction the pump produces a relatively high suction pressure in the order of about 1300 mm water head which subsequently falls steadily until the middle of the suction stroke is reached where the pressure has been reduced to about 800 mm water head. During the remaining part of the suction stroke the pressure initially increases slightly as indicated and then it falls and rises again to about 1850 mm water head and finally it falls vigorously, viz. when the suction stroke ends. However, the above mentioned variation in suction pressure does not exceed what can reasonably be tolerated for the purpose explained above. The abrupt increase at the end of the suction stroke is very short in relation to the time during which the suction stroke is effective and is caused by the straightening out of the central part of the pump body 2 before reaching the configuration shown in FIG. 6.

I claim:

1. A suction pump for draining body fluids from body cavities, said suction pump comprising a bottom portion having a rim and a domed resilient pump body having a substantially smooth inner surface, said pump body being connected to the bottom portion along said rim and forming a pumping chamber between the bottom portion and pump body, said suction pump further comprising an inlet valve and an outlet valve, said resilient pump body being resiliently deformable by manual action from its domed configuration towards the bottom portion for the provision of the pressure stroke of the suction pump and due to its elasticity returning to its domed configuration when relieved for the provision of the suction stroke of the pump, wherein the bottom portion has a surface which faces said pumping chamber and which is substantially continuous and concave in a central area thereof to correspond with an inner configuration of the pump body in the deformed state thereof to enable substantially the entire pumping chamber volume to provide a pumping function.

2. A suction pump according to claim 1, wherein in the domed state of the pump body the inner surface of the pump body substantially has the form of a spherical segment.

3. A suction pump according to claim 2, wherein the spherical segment has an arc measure ranging between about 100° and about 140°.

4. A suction pump according to claim 2, wherein at a top thereof the spherical segment has a slightly smaller radius of curvature than at its sides.

5. A suction pump according to claim 1, wherein the inlet valve and the outlet valve are offset on the same side of a central plane defined by the rim of the pump body and are connected to the pump chamber through channels in the concave portion of the bottom portion.

6. A suction pump according to claim 3, wherein said arc measure is between about 110° to 130°.

7. A suction pump according to claim 6, wherein said arc measure is about 120°.

8. A suction pump according to claim 1, wherein said surface of said bottom portion is substantially spherical in said central area thereof.

* * * * *